United States Patent
Goldberg et al.

(10) Patent No.: US 10,034,895 B2
(45) Date of Patent: Jul. 31, 2018

(54) LOCAL APPLICATION OF D-LACTIC ACID DIMER IS SELECTIVELY CYTOTOXIC WHEN APPLIED TO CANCER CELLS

(71) Applicants: Joel Steven Goldberg, Hillsborough, NC (US); Joe Brice Weinberg, Durham, NC (US)

(72) Inventors: Joel Steven Goldberg, Hillsborough, NC (US); Joe Brice Weinberg, Durham, NC (US)

(73) Assignee: Joel Steven Goldberg, Hillsborough, NC (US)

( * ) Notice: Subject to any disclaimer, the term of this patent is extended or adjusted under 35 U.S.C. 154(b) by 0 days.

(21) Appl. No.: 15/827,958

(22) Filed: Nov. 30, 2017

(65) Prior Publication Data

US 2018/0085394 A1 Mar. 29, 2018

(51) Int. Cl.
*A61K 9/00* (2006.01)
*A61K 31/765* (2006.01)
*C08G 63/06* (2006.01)

(52) U.S. Cl.
CPC ............ *A61K 31/765* (2013.01); *C08G 63/06* (2013.01)

(58) Field of Classification Search
CPC .................................................. A61K 31/765
See application file for complete search history.

(56) References Cited

U.S. PATENT DOCUMENTS

| | | | |
|---|---|---|---|
| 8,920,789 B2 | 12/2014 | Goldberg | |
| 9,382,376 B2 | 7/2016 | Goldberg | |
| 2005/0187186 A1* | 8/2005 | Maurer | A61K 9/0019 514/54 |
| 2008/0262150 A1* | 10/2008 | Takenaka | C08J 3/201 524/599 |
| 2012/0195850 A1* | 8/2012 | Goldberg | A61K 31/765 424/78.37 |

OTHER PUBLICATIONS

Burt, Controlled Delivery of Taxol from Microspheres Composed of a Blend Ethylene-Vinyl Acetate Copolymer and Poly(d-lactide), Cancer Letters, 1995, 88, 73-79.*
Goldberg, JS PDLA a potential new potent analgesic: a case report Local and regional anesthesia. 2014:7:59-61.
Goldberg, JS Stereocomplexes formed from selelct oligomers of Pdla . . . Applications of the Warburg Effect, Perspectives Med Chem, 2011:5 1-10.
U.S. Appl. No. 15/182,481, filed Jul. 2, 2015, Goldberg, JS.
U.S. Appl. No. 15/182,553, filed Jul. 2, 2015, Goldberg, JS.

\* cited by examiner

*Primary Examiner* — Paul W Dickinson

(57) ABSTRACT

At equimolar concentrations, D-lactic acid dimer is more cytotoxic than L-lactic acid when directly applied to human HeLa cells in culture. The cytotoxicity of D-lactic acid dimer is an independent effect exclusive of the lower pH when applied to cancer cells in culture. At equimolar concentrations, D-lactic acid dimer is less cytotoxic than L-lactic acid when applied to normal human fibroblasts in culture. D-lactic acid dimer is cytotoxic when applied to human retinoblastoma cells in culture in a dose-dependent fashion. The experimental data supports the cytotoxic mechanism of D-lactic acid dimer via the Warburg effect.

1 Claim, 16 Drawing Sheets

LOCAL APPLICATION OF D-LACTIC ACID DIMER IS SELECTIVELY CYTOTOXIC WHEN APPLIED TO CANCER CELLS

CROSS-REFERENCES TO RELATED APPLICATIONS

None

FEDERALLY FUNDED RESEARCH

None

BACKGROUND OF THE INVENTION

Discovery of a new chemical reaction, a fundamental property of nature, is a major finding. For example, without the discovery of the Haber process, which resulted in nitrogen fixation, modern fertilizers could not be manufactured, and the current world population growth would not be sustainable.

In 2011, at Duke University and the Durham Va. Medical Center, we discovered that a stereocomplex chemical reaction occurred between L-lactate and Polymer D-lactic acid (PDLA). (Goldberg, Weinberg 2014, 2016) A stereocomplex is a new substance that is formed when a molecule and its mirror image (D and L or enantiomers) come together with the proper orientation. The reaction occurs spontaneously and rapidly without a catalyst or enzyme. Later we discovered that D-lactic acid dimer (two D-lactic acids connected by an ester bond), synthesized at the Duke Small Molecule Synthesis Facility, would "sequester or trap" L-lactate.

L-lactate has many potential functions. It can act as a neurotransmitter, a buffer for the efflux of hydrogen ions in some cancer cells, and an intermediary in glycolysis. Otto Warburg, a preeminent biochemist of the $20^{th}$ century who was nominated for 51 Nobel Prizes, discovered that most cancer cells utilize the glycolytic pathway to produce ATP (the "Warburg effect"). This discovery led to the common use of positron emission tomomgraphy (PET) scans for imaging cancer in vivo.

In normal cells, most glucose is metabolized by three separate but linked pathways (glycolysis, the Krebs cycle, and oxidative phosphorylation) to produce ATP. Final products of glycolysis include hydrogen ions that are effluxed from the cell. These hydrogen ions must be buffered to maintain electrical neutrality in the cell, and one of those buffering ions is often L-lactate. In a normal cell, the hydrogen ion produced from glycolysis is primarily passaged to oxidative phosphorylation, but many cancer cells do not have that option. Therefore, it would seem that sequestering L-lactate would have significant biologic effects on those cancer cells which depend upon glycolysis for generation of ATP.

We believe that D-lactic acid dimer would be unlikely to produce effects as a systemically administered drug, because the concentration required to form the stereocomplex is not realistically obtainable by the oral or parenteral route. However, local application of the D-lactic acid dimer onto or into tumors could be tumoricidal and useful as a debulking agent. Local application of chemotherapeutic drugs has been performed during neurosurgery where topical application of carmustine implants, Gliadel® Wafers, treat glioblastomas. (Perry et al 2007)

There are other potential uses of D-lactic acid dimer. These include local application to nerves for analgesia and local application to areas of high rates of glycolysis such as occur in *Plasmodium* aggregates. (Goldberg 2014, 2015, 2015)

We previously showed that oligomers of PDLA have cytotoxic properties when incubated with fresh leukemia cells compared to a control of Polymer L-lactic acid (PLLA). However, the cytotoxicity occurred at low pH (~4), which obscured the findings. (Goldberg, Weinberg 2014, 2016)

This invention is an improvement over previous inventions. It definitively demonstrates that local application of D-lactic acid dimer to cultured cancer cells kills the cancer cells, and the killing is independent of the changes in pH when the dimer is applied. This invention demonstrates that D-lactic acid dimer could debulk the vast majority of tumors that depend upon glycolosis for production of ATP.

DESCRIPTION OF THE DRAWINGS

All photomicrographs were obtained under 100× power through an inverted microscope.

FIG. 1 shows cultured HeLa cells treated with 10 mg of D-lactic acid dimer and stained with trypan blue. The cells are 100% non-viable.

FIG. 2 shows cultured HeLA cells treated with 5 mg of D-lactic acid dimer and stained with trypan blue. The cells are 80% non-viable.

FIG. 3 shows cultured HeLa cells treated with 5 mg of PLLA and stained with trypan blue. Less than 5% of the cells are non-viable.

FIG. 4 shows cultured HeLA cells that have been treated with 5 mg of L-lactic acid and stained with trypan blue. In solution, 5 mg of L-lactic acid has approximately the same hydrogen ion concentration as 10 mg of D-lactic acid dimer. The cytotoxic effects of D-lactic acid dimer is independent of pH effects when compared to FIG. 1. Zero percent of the cells are non-viable.

FIG. 5 shows cultured HeLa cells that have been treated with 2.5 mg of L-lactic acid and stained with trypan blue. In solution, 2.5 mg of L-lactic acid has approximately the same hydrogen ion concentration as 5 mg of D-lactic acid dimer. The cytotoxic effect of D-lactic acid dimer is independent of pH effects when compared to FIG. 2. Zero percent of the cells are non-viable.

FIG. 6 shows cultured HeLa cells that have received no treatment and are stained with trypan blue. Zero percent of the cells are non-viable.

FIG. 7 shows human retinoblastoma cells treated with 25 mg of D-Lactic acid dimer and stained with trypan blue. Fifty percent of the cells are non-viable.

FIG. 8 shows human retinoblastoma cells treated with 12.5 mg of D-lactic acid dimer and stained with trypan blue. Fifty percent of the cells are non-viable.

FIG. 9 shows human retinoblastoma cells treated with 6.25 mg of D-Lactic acid dimer and stained with trypan blue. Thirty percent of the cells are non-viable.

FIG. 10 shows human retinoblastoma cells treated with 3.13 mg of D-lactic acid dimer and stained with trypan blue. Zero percent of the cells are non-viable.

FIG. 11 shows human retinoblastoma cells treated with 1.5 mg of D-lactic acid dimer and stained with trypan blue. Zero percent of the cells are non-viable.

FIG. 12 shows human retinoblastoma cells with no treatment and stained with trypan blue. Zero percent of the cells are non-viable

Table 1 is a summary of the figures.

TABLE 1

Trypan blue viability studies of HeLa, retinoblastoma, and normal fibroblast cells

| FIG. | Cell type | Drug administered | Trypan blue staining for non-viable cells |
|---|---|---|---|
| 1 | HeLa | 10 mg D-lactic acid dimer | 100% cells non-viable |
| 2 | HeLa | 5 mg D-lactic acid dimer | 80% cells non-viable |
| 3 | HeLa | 5 mg PLLA | less than 5% cells non-viable |
| 4 | HeLa | 5 mg L-lactic acid | 0% cells non-viable |
| 5 | HeLa | 2.5 mg L-lactic acid | 0% cells non-viable |
| 6 | HeLa | no treatment | 0% cells non-viable |
| 7 | Retinoblastoma | 25 mg D-lactic acid dimer | 50% cells non-viable |
| 8 | Retinoblastoma | 12.5 mg D-lactic acid dimer | 50% cells non-viable |
| 9 | Retinoblastoma | 6.25 mg D-lactic acid dimer | 30% cells non-viable |
| 10 | Retinoblastoma | 3.13 mg D-lactic acid dimer | 0% cells non-viable |
| 11 | Retinoblastoma | 1.5 mg D-lactic acid dimer | 0% cells non-viable |
| 12 | Retinoblastoma | no treatment | 0% cells non-viable |
| 13 | Fibroblast | 6 mg D-lactic acid dimer | 0% cells non-viable |
| 14 | Fibroblast | 6 mg L-lactic acid | 100% cells non-viable |
| 15 | Fibroblast | 3.13 mg D-lactic acid dimer | 0% cells non-viable |
| 16 | Fibroblast | 3.13 mg L-lactic acid | 40% cells non-viable |

DETAILED DESCRIPTION OF THE INVENTION

When high concentrations of D-lactic acid dimer and L-lactate are mixed, a spontaneous, rapid, non-enzymatic reaction results which produces a sterocomplex at biologic temperatures.

Approximately 1.0-1.5 moles of D-lactic acid dimer are required to sequester 1 mole of L-lactic acid. (Table 2, Experiment 1) Achieving such a high concentration of D-lactic acid dimer via oral or parenteral administration may not be possible without unacceptable toxicities. Therefore, we discovered that local application of D-lactic dimer into or onto cancer cells would be cytotoxic, and this cytotoxicity is independent of the decrease in pH from the carboxylic acid group of D-lactic acid dimer.

Figure 1:
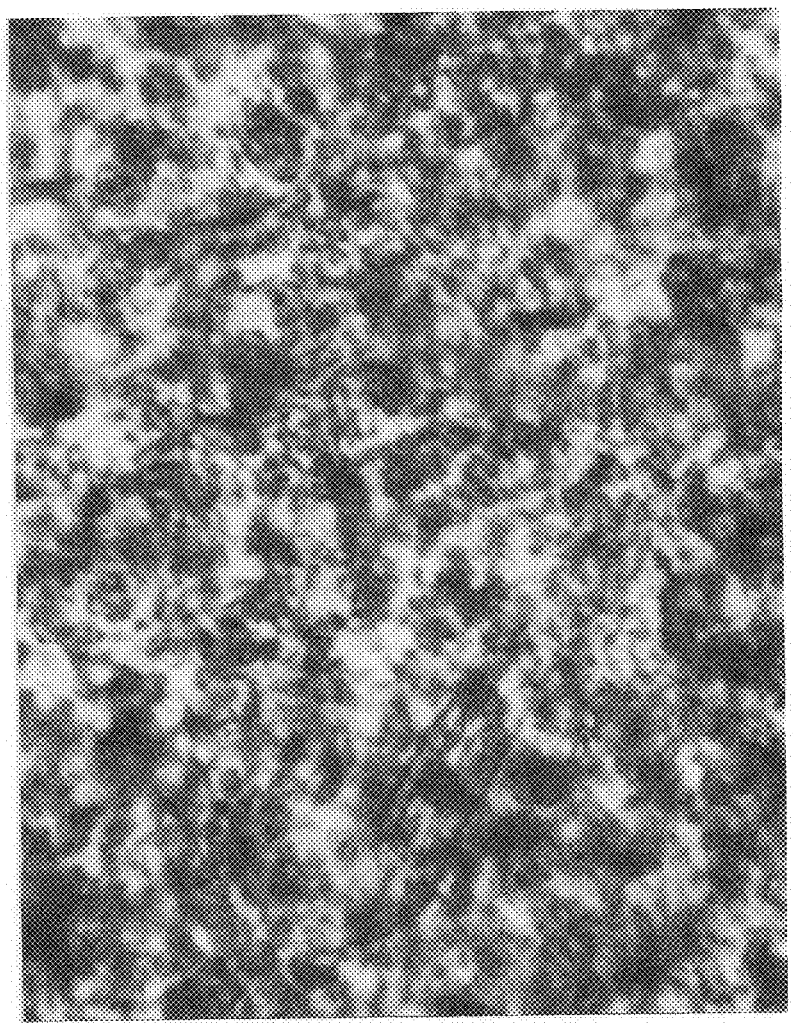
FIGS. 1-6 show treatment of HeLa cells with D-lactic acid dimer, L-lactic acid, and PLLA.
Figure 2:
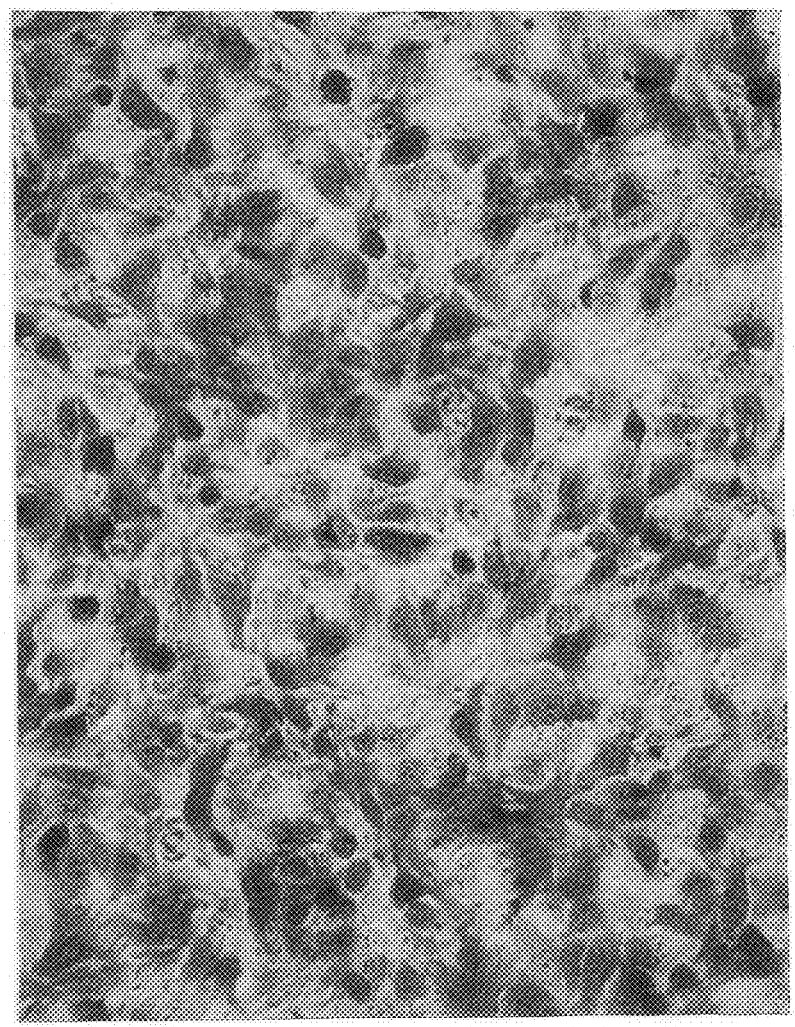
Figure 3:
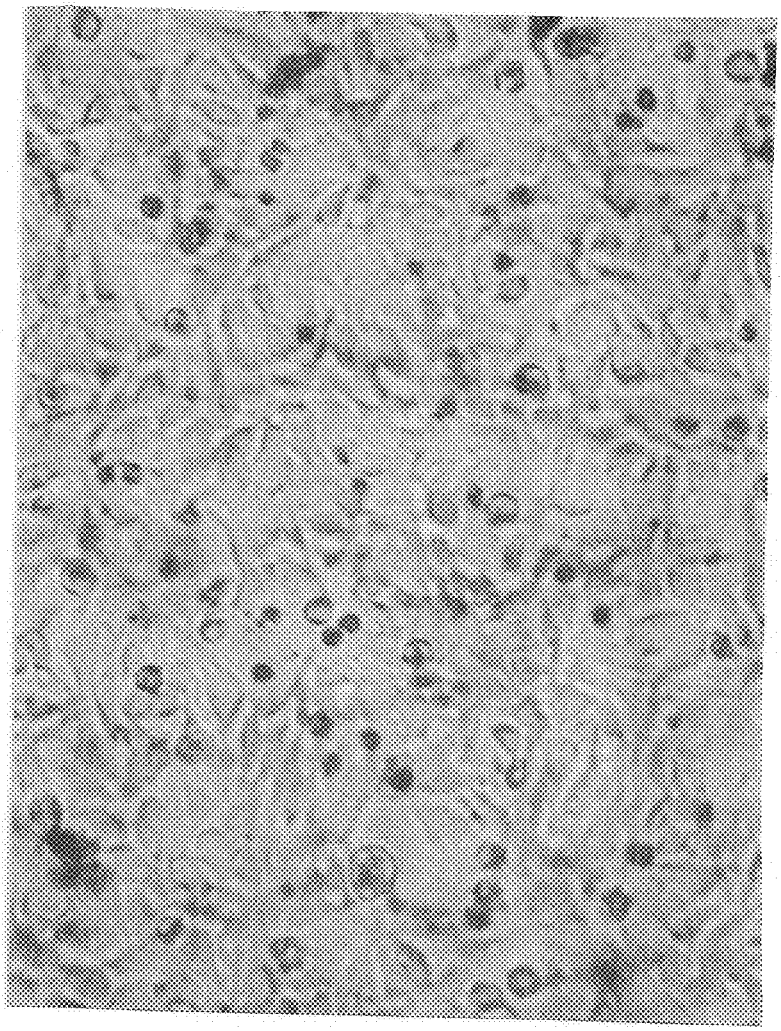
Figure 4:
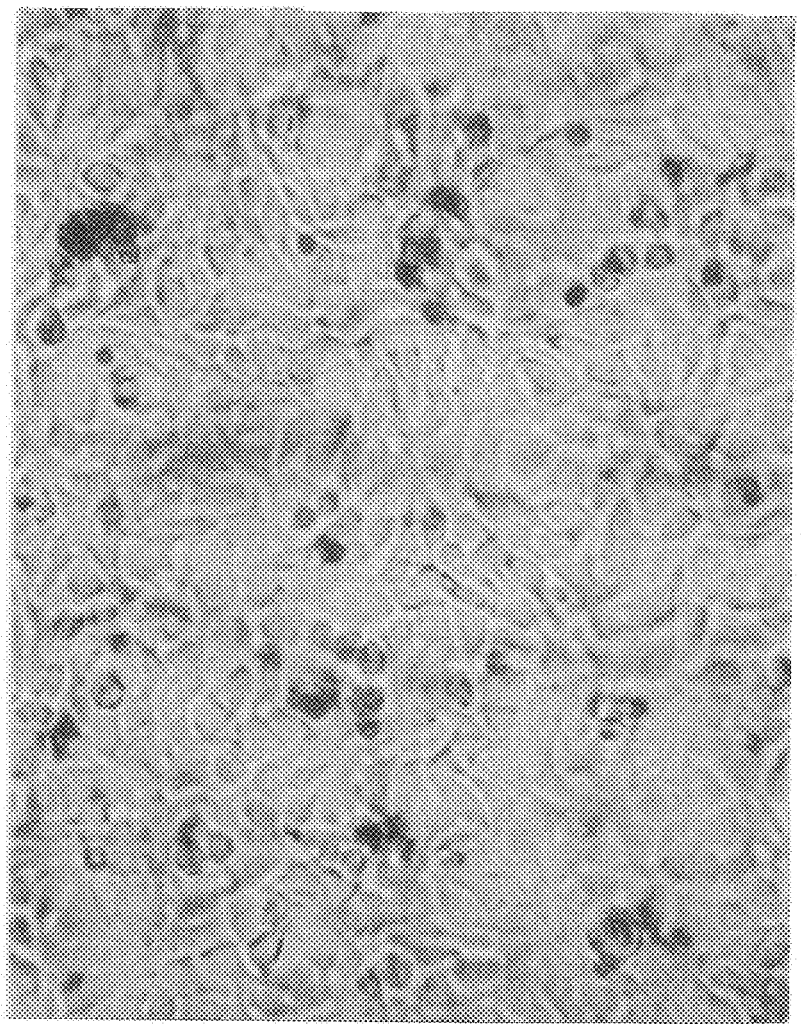
Figure 5:
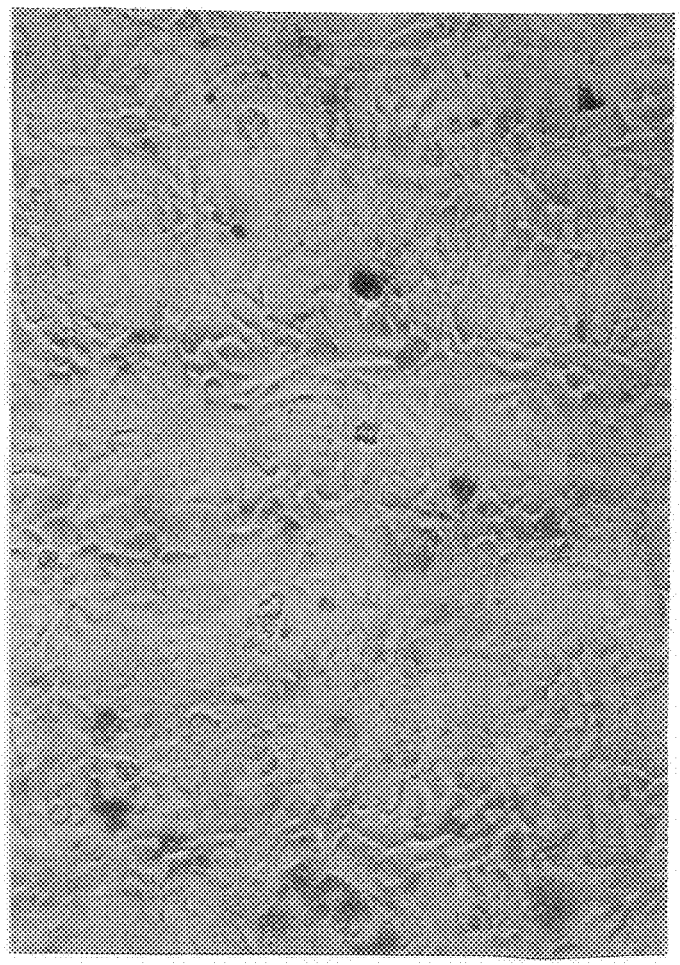
Figure 6:
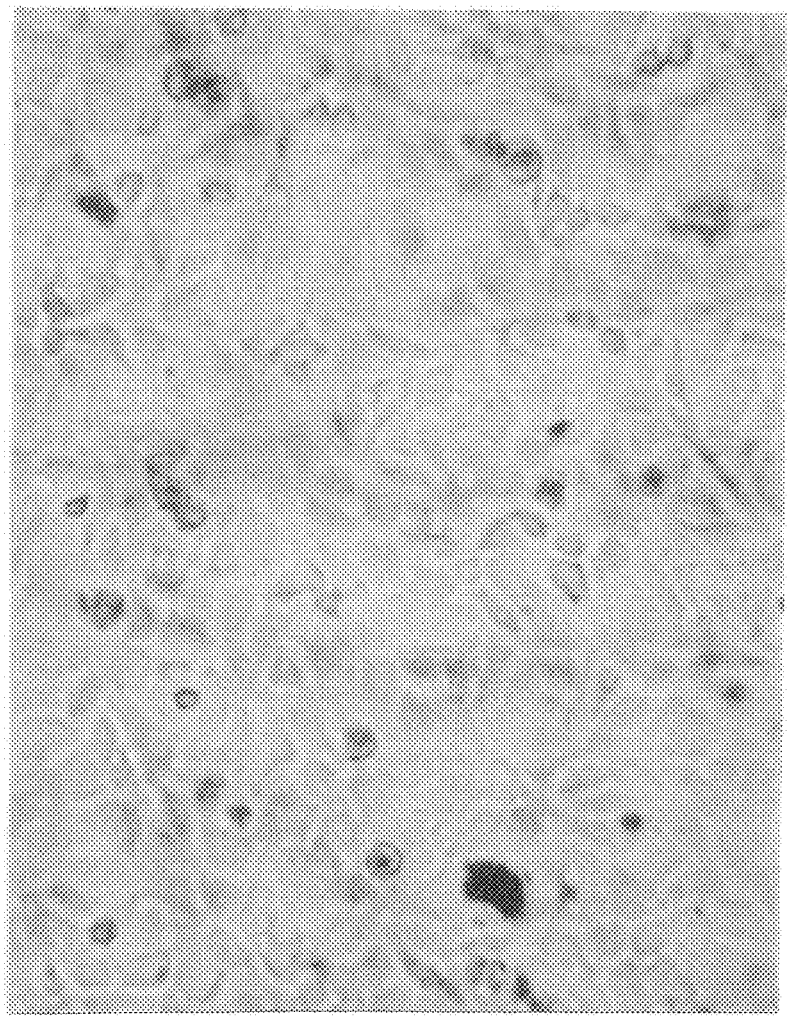
Figure 7:
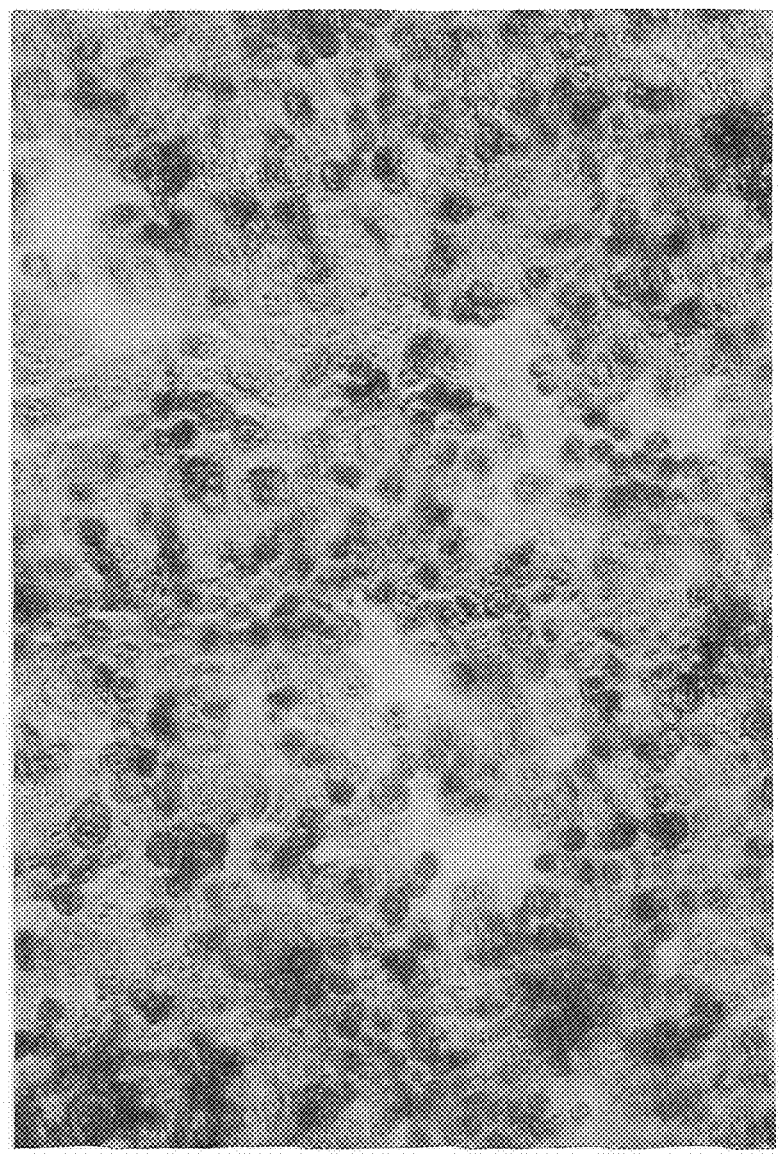
FIGS. 7-12 show the dose response effects of D-lactic acid dimer treatment to human retinoblastoma cells.
Figure 8:
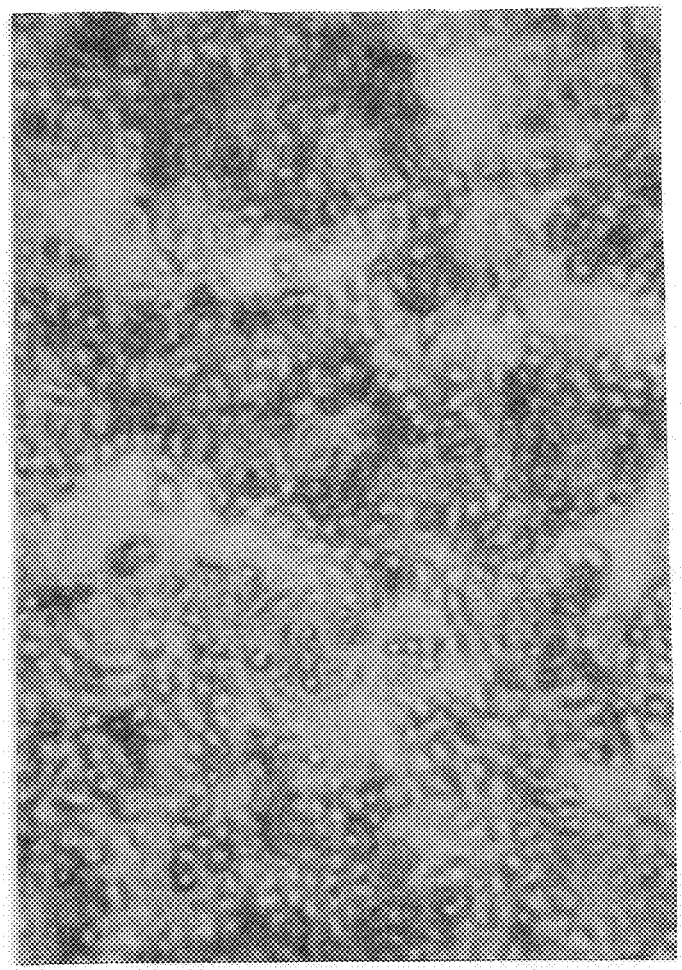
Figure 9:
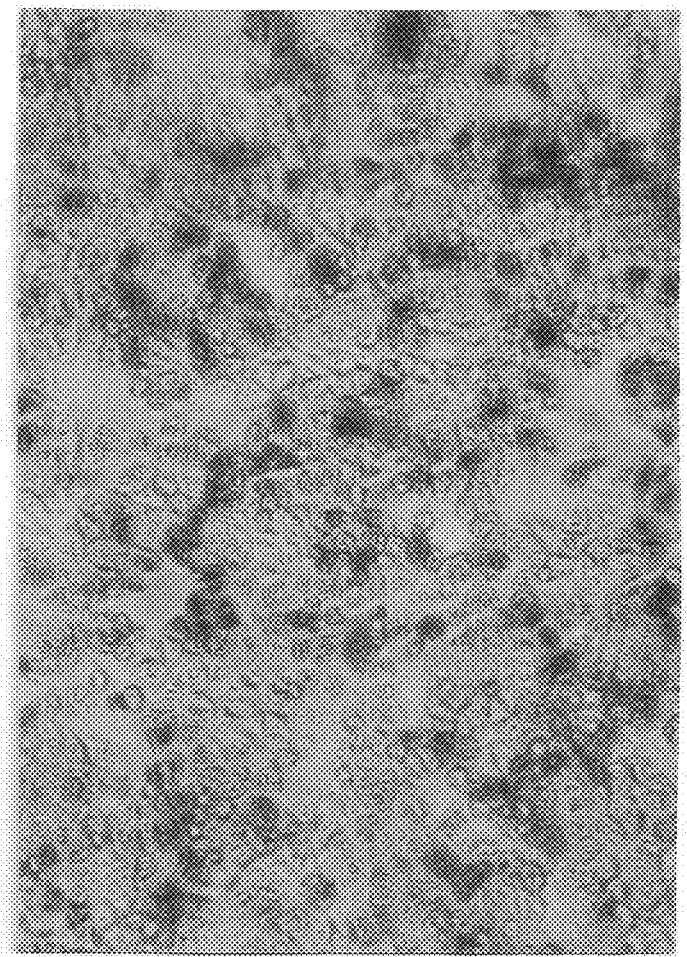
Figure 10:
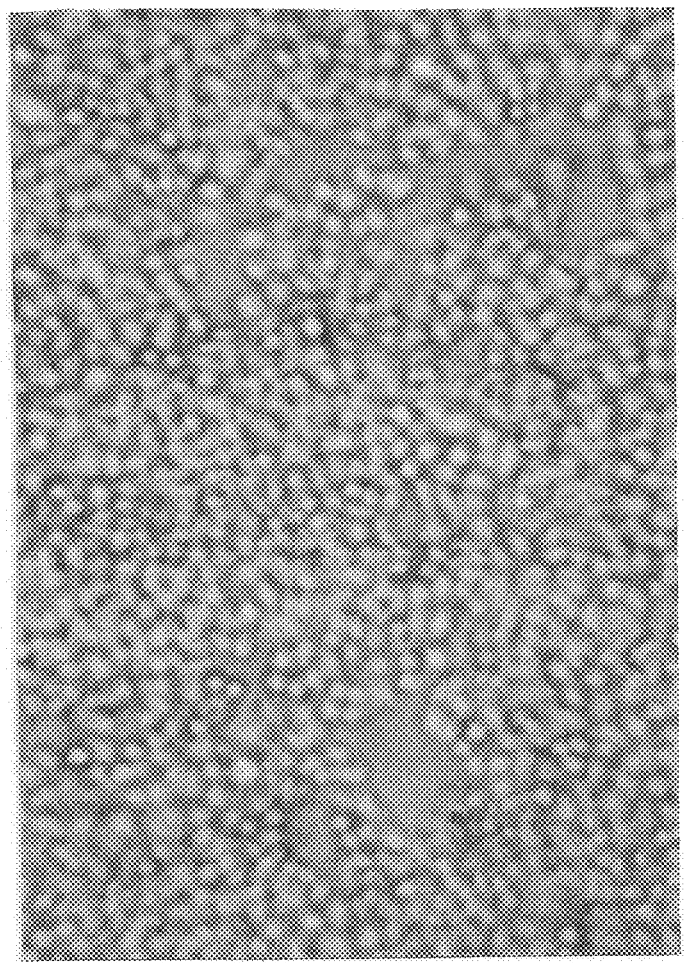
Figure 11:
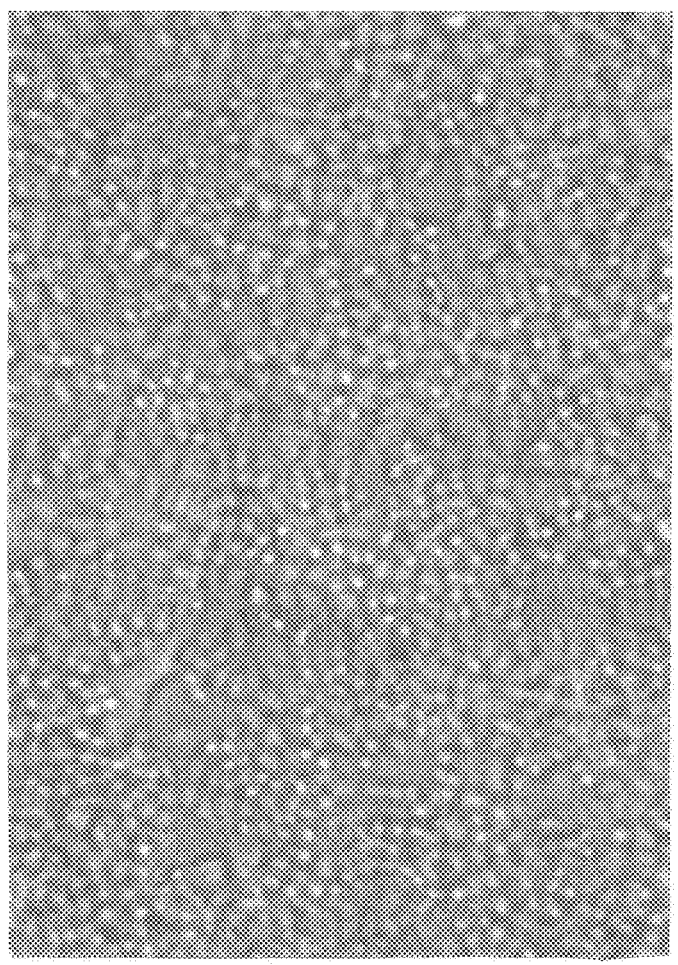
Figure 12:
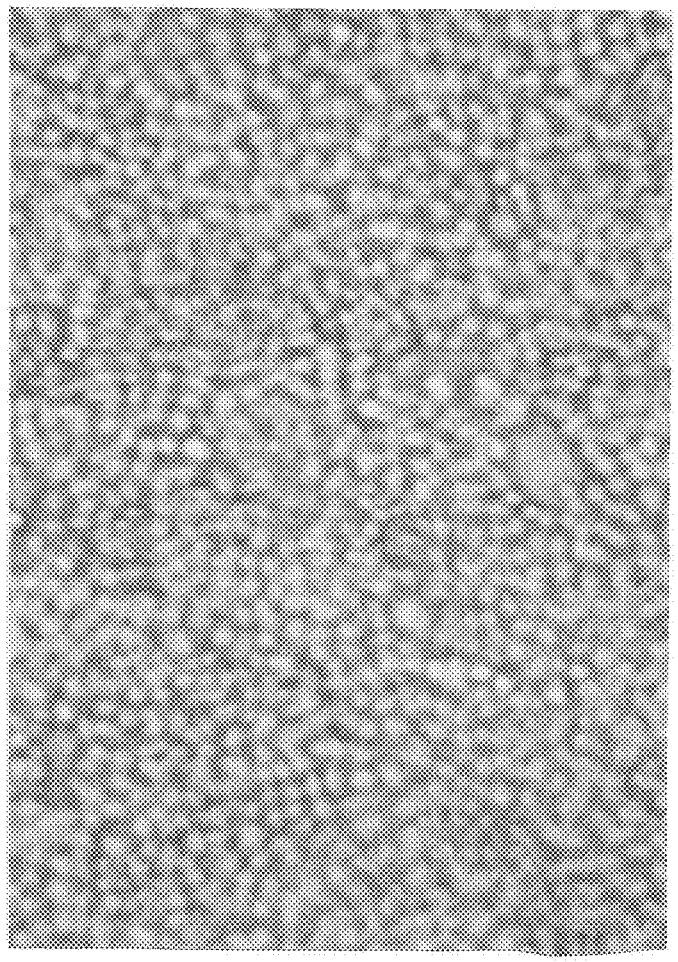

In our previous invention, we showed that PDLA was more cytotoxic than PLLA. In this invention, we confirm that D-lactic acid dimer is more cytotoxic than a mixture of PLLA oligomers when applied to cultured HeLa cells. (FIGS. 2 & 3, Experiment 2)

We also demonstrated the cytotoxic dose response to D-Lactic acid dimer when applied to human retinoblastoma cells and an effective cytotoxic dose greater than 6.25 mg/ml. (FIGS. 7-12, Experiment 3)

In addition, we demonstrated that the D-lactic acid dimer is less cytotoxic on a molar basis than L-lactic acid when applied to cultured normal fibroblasts. (FIGS. 13-16, Experiment 4) Thus, the cytotoxicity of D-lactic acid dimer is cancer specific and consistent with the Warburg effect as its mechanism of action.

Benefits to Society

Sequestration of L-lactate by D-lactic acid dimer or larger oligomers may have important biological significance since L-lactate is essential for neurotransmission, as an intermediary of glycolysis, as an energy source, and as a buffer in cancer cells. Previously, it was thought that D-lactic acid dimer could be systemically administered for biologic effects. However, it is more likely that formation of the stereocomplex that sequesters L-lactate without a catalyst and at biologic temperatures is a chemical reaction that will occur with very high concentrations of D-lactic acid dimer.

It has been shown that the tetramer oligomer (n=4) of D-lactic acid does not sequester L-lactate, and the model would predict such because two L-lactate molecules may not template onto the tetramer because of steric hindering. We postulate that the n=5 or n=6 oligomers may be cytotoxic and have drug-like properties according to Lipinski criteria. If this is true, these oligomers would be more potent cancer medications, opening up the possibility for systemic administration.

EXPERIMENTAL DATA

D-lactic acid dimer was synthesized by Dr. David M. Gooden at the Small Molecule Synthesis Facility, Duke University, Durham, N.C. Cells for culture were obtained from the Cell Culture Facility at Duke University. PLLA was microwave synthesized from L-lactic acid as previously reported. Lactic acid concentration was measured by tetrazolium indicator color test strips (Accuvin, LLC, Napa, Calif.) from the reaction of L-lactic acid and nicotineadenine in the presence of lactate dehydrogenase. All cells were cultured at 37° C. and 5% $CO_2$ in a HERA cell incubator (Kendro Laboratory Products, L.P., Newtown, Conn.). Media for cells was Minimum Essential Media with Earl's salts and L-Glutamine (Gibco, Life Technologies) with 10% fetal bovine serum and non-essential amino acids and sodium pyruvate. Antibiotics for experiment #2 were penicillin/streptomycin and for experiments #3-4 were penicillin/streptomycin/amphotericin B. All drug testing was performed in Costar 6 Well Culture Cluster plates (Corning, Corning, N.Y.). The trypan blue concentration was 0.4%.

Experiment #1

Stoichiometry of the L-Lactic Acid+D-Lactic Acid Dimer Stereocomplex Reaction D-lactic acid dimer is a thick viscous liquid with a consistency of honey. Samples of D-lactic acid dimer were weighed on truncated 100 micro liter pipette tips. The tips were then inserted into the pipette, and D-lactic acid dimer was mixed in 40 micro liters of 10 mM L-lactic acid. The reactions were carried out at room temperature and allowed to incubate for two minutes after which 20 microliters were applied to L-lactic acid test strips, and the results were read after two minutes. The molar ratio of D-lactic acid dimer (MW 162 g/mol) to L-lactic acid (MW 90 g/mol) ~0.004/0.004-0.006/0.004 for complete sequestration of L-lactic acid. (Table 2)

TABLE 2

Stereocomplex reaction of L-lactic acid + D-lactic acid dimer

| Lactic acid | D-lactic acid dimer | Tetrazolium indicator |
|---|---|---|
| 40 microliters of 10 mM | 0 mg | greater than 400 mg/L |
| 40 microliters of 10 mM | 0.5 mg D-lactic acid dimer | 80 mg/L |
| 40 microliters of 10 mM | 1.0 mg D-lactic acid dimer | no color change |
| 40 microliters of 10 mM | 5.0 mg D-lactic acid dimer | no color change |
| 40 microliters of 10 mM | 7.0 mg D lactic acid dimer | no color change |

Experiment #2

Cytotoxicity of D-Lactic Acid Dimer Compared to L-Lactic Acid and PLLA

HeLa cells (ATCC CCL-2) were cultured on six well plates. At 50-80% confluency, the media was exchanged to 1 ml of media for each well, and after two hours of incubation, D-lactic acid dimer, PLLA, or lactic acid were added to the wells. The cells were incubated for 12 hours, after which time they were stained with 1 ml trypan blue for two minutes. The media and trypan blue were aspirated from each well, and the cells were then placed under an inverted microscope for photography. (Table 3)

TABLE 3

HeLa cell cytotoxicity testing

| FIGS. | Dose | Cell characteristics |
|---|---|---|
| 1 | 10 mg or 0.062 mmole D-lactic acid dimer | 100% cells non-viable |
| 2 | 5 mg or 0.031 mmole D-lactic acid dimer | 80% cells non-viable |
| 3 | 5 mg PLLA | less than 5% cells non-viable |
| 4 | 5 mg or 0.055 mmole L-lactic acid | 0% cells non-viable |

TABLE 3-continued

HeLa cell cytotoxicity testing

| FIGS. | Dose | Cell characteristics |
|---|---|---|
| 5 | 2.5 or 0.028 mmole mg L-lactic acid | 0% cells non-viable |
| 6 | No treatment | 0% cells non-viable |

Conclusion: D-lactic acid dimer is cytotoxic when applied to HeLa cells at concentrations of 5 mg/ml or more, and this effect is independent of effect from hydrogen ion concentration. D-lactic acid dimer is more cytotoxic than PLLA, which is consistent with earlier findings. These results are consistent with sequestration of L-lactate as a cytotoxic mechanism of action of D-lactic acid dimer and with the Warburg effect.

Experiment #3

D-Lactic Acid Dimer Dose Response Relationship when Applied to Human Retinoblastoma Cells Human retinoblastoma cells (ATCC C-33A) were cultured in six well plates. At 50-80% confluency, the medium was exchanged to 1 ml of fresh media for each well, and after two hours of incubation, concentrations of D-lactic acid dimer were added to the wells. The cells were incubated for 12 hours after which time they were stained with 1 ml trypan blue for two minutes. The media and trypan blue were aspirated from each well, and the cells were examined with an inverted microscope for photography. (Table 4)

TABLE 4

Retinoblastoma cytotoxicity testing

| FIG. | Dose | Cell characteristic |
|---|---|---|
| 7 | 25 mg or 0.154 mmole D-lactic acid dimer | 50% cells non-viable |
| 8 | 12.5 mg or 0.077 mmole D-lactic acid dimer | 50% cells non-viable |
| 9 | 6.25 mg or 0.039 mmole D-lactic acid dimer | 30% cells non-viable |
| 10 | 3.13 mg or 0.019 mmole D-lactic acid dimer | 0% cells non-viable |
| 11 | 1.5 mg or 0.009 mmole D-lactic acid dimer | 0% cells non-viable |
| 12 | no treatment | 0% cells non-viable |

Conclusion: D-lactic acid dimer is cytotoxic when applied to human retinoblastoma cells at concentrations greater than 6.25 mg/ml.

Experiment #4

Normal human fibroblast cells (ATCC CCL-171) were subcultured onto six well plates. At 50-80% confluency, the media was exchanged to 1 ml of media for each well, and after two hours of incubation, concentrations of D-lactic acid dimer or L-lactic were added to the wells. The cells were incubated for 12 hours after which time they were stained with 1 ml trypan blue for two minutes. The media and trypan blue were aspirated from each well, and the cells were then placed under an inverted microscope for photography. (Table 5)

| Well or FIG. | Dose | Cell characteristic |
|---|---|---|
| Well 1 | 25 mg or 0.154 mmole D-lactic acid dimer | 100% cells non-viable |
| Well 2 | 25 mg or 0.277 mmole L-lactic acid | 100% cells non-viable |
| Well 3 | 12.5 mg or 0.077 mmole D-lactic acid dimer | 100% cells non-viable |
| Well 4 | 12.5 mg or 0.139 mmole L-lactic acid | 100% cells non-viable |

-continued

Figure 13:
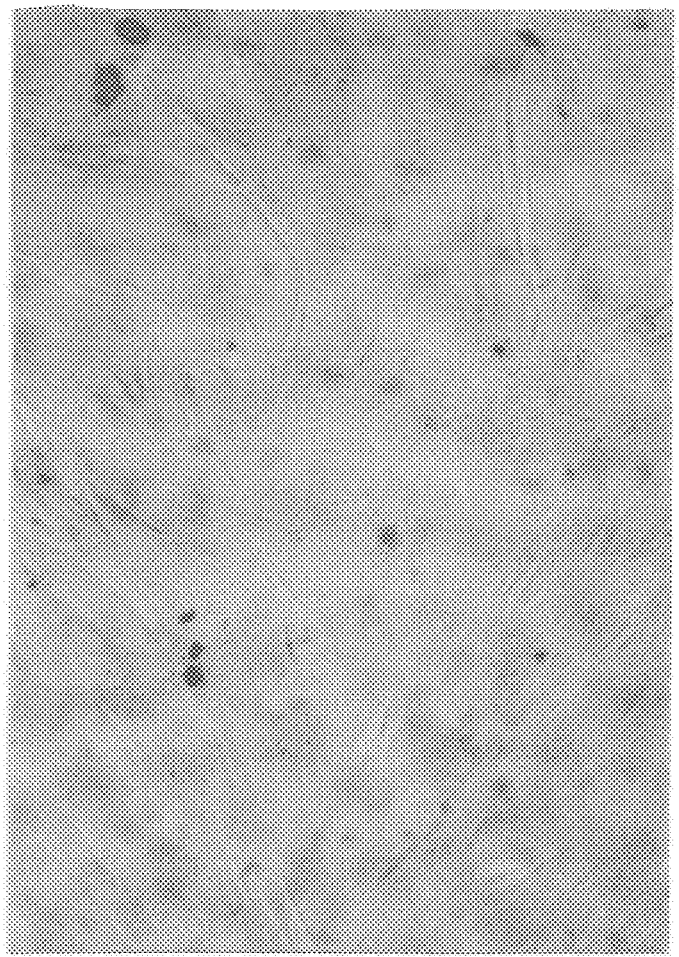
FIG. 13 shows normal human fibroblast cells treated with 6 mg of D-lactic acid dimer. Zero percent of the cells are non-viable.
Figure 14:
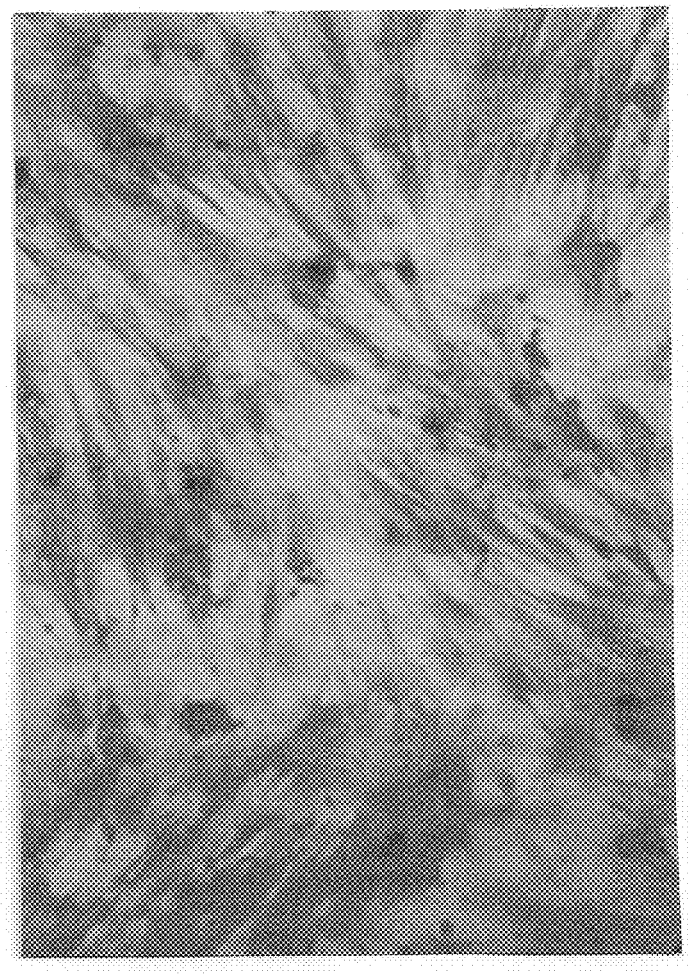
FIG. 14 shows normal human fibroblasts treated with 6 mg of L-lactic acid. One hundred percent of the cells are non-viable.
Figure 15:
FIG. 15 shows normal human fibroblasts treated with 3.13 mg of D-lactic acid dimer. Zero percent of the cells are non-viable.
Figure 16:
FIG. 16 shows normal human fibroblasts treated with 3.13 mg of L-lactic acid. Forty percent of the cells are non-viable.

| Well or FIG. | Dose | Cell characteristic |
|---|---|---|
| FIG. 13 | 6.25 mg or 0.039 mmole D-lactic acid dimer | 0% cells non-viable |
| FIG. 14 | 6.25 mg or 0.070 mmole L-lactic acid | 100% cells non-viable |
| FIG. 15 | 3.13 mg or 0.020 mmole D-lactic acid dimer | 0% cells non-viable |
| FIG. 16 | 3.13 mg or 0.035 mole L-lactic acid | 40% cells non-viable |
| Well 9 | 1.50 mg or 0.009 mmole D-lactic acid dimer | 0% cells non-viable |
| Well 10 | 1.50 mg or 0.016 mole L-lactic acid | 0% cells non-viable |

Conclusion: L-lactic acid is more cytotoxic than D-lactic acid dimer when applied to normal cultured fibroblasts.

SUMMARY

1. D-lactic acid dimer is selectively cytotoxic when locally applied to cancer cells at a concentration of 5.00 to 6.25 mg/ml or greater.
2. D-lactic acid dimer has cytotoxic effects distinct from its effect on pH.
3. Equimolar concentrations of D-lactic acid dimer are less cytotoxic than L-lactic acid when applied to normal cells.
4. The mechanism of cytotoxic action of D-lactic acid dimer is consistent with sequestration of L-lactate and the Warburg effect.

REFERENCES

Goldberg, J. S., Weinberg, J. B. (2014). U.S. Pat. No. 8,920,789 B2. Washington, D.C.: USPTO Goldberg, J. S., Weinberg, J. B. (2016). U.S. Pat. No. 9,382,376 B2. Washington, D.C.: USPTO Perry J, Chambers A, Spithoff K, Laperriere N. Gliadel wafers in the treatment of malignant glioma: a systematic review. Current oncology. October 2007; 14(5): 189-194.

Goldberg, J. S. (2015) U.S. patent application Ser. No. 15/018,2481 A1. Washington, D.C.: USPTO Goldberg, J. S. (2015) U.S. patent application Ser. No. 15/018,2553 A1. Washington, D.C.: USPTO Goldberg J. S. PDLA a potential new potent topical analgesic: a case report. Local and regional anesthesia. 2014;7:59-61.

Having described our invention, we claim:

1. A method of treating cancer in a subject comprising administering to said subject a composition comprising D-lactic acid dimer.

* * * * *